(12) United States Patent
Kurp

(10) Patent No.: US 7,914,682 B2
(45) Date of Patent: Mar. 29, 2011

(54) METHOD FOR REMOVING IMPURITIES FROM A UREA SOLUTION

(75) Inventor: Ronald Daniel Kurp, Shamong, NJ (US)

(73) Assignee: Colonial Chemical Company, Tabernacle, NJ (US)

( * ) Notice: Subject to any disclaimer, the term of this patent is extended or adjusted under 35 U.S.C. 154(b) by 335 days.

(21) Appl. No.: 12/231,206

(22) Filed: Aug. 29, 2008

(65) Prior Publication Data

US 2009/0057230 A1   Mar. 5, 2009

Related U.S. Application Data

(60) Provisional application No. 60/966,617, filed on Aug. 29, 2007.

(51) Int. Cl.
    *C02F 1/42* (2006.01)
(52) U.S. Cl. ......... 210/660; 210/670; 210/681; 210/691
(58) Field of Classification Search .................. 210/660, 210/670, 681, 691
    See application file for complete search history.

(56) References Cited

U.S. PATENT DOCUMENTS

| | | |
|---|---|---|
| 3,903,158 A | 9/1975 | Fuentes et al. |
| 4,043,938 A | 8/1977 | Reif et al. |
| 4,048,055 A | 9/1977 | Wegner et al. |
| 4,188,292 A | 2/1980 | Fitzgibbons |
| 4,346,067 A | 8/1982 | Wachter |
| 3,903,158 A | 2/1984 | Fuentes et al. |
| 4,645,750 A | 2/1987 | Best |
| 4,645,860 A | 2/1987 | Green, II et al. |
| 4,650,901 A | 3/1987 | Young et al. |
| 4,654,442 A | 3/1987 | Young et al. |
| 4,658,059 A * | 4/1987 | Young et al. .................... 564/73 |
| 4,672,078 A | 6/1987 | Sakai et al. |
| 4,698,443 A | 10/1987 | Young et al. |
| 4,701,555 A | 10/1987 | Young et al. |
| 4,721,652 A | 1/1988 | Takai et al. |
| 5,314,852 A | 5/1994 | Klatte |
| 5,567,666 A | 10/1996 | Beck et al. |
| 6,838,069 B2 | 1/2005 | Blonigen et al. |
| 7,108,784 B1 | 9/2006 | Litz et al. |
| 7,198,785 B2 | 4/2007 | O'Loughlin et al. |

FOREIGN PATENT DOCUMENTS

| | | |
|---|---|---|
| JP | 61171506 A | 8/1986 |
| JP | 2006068680 | 3/2006 |
| JP | 2008239574 | 10/2008 |

OTHER PUBLICATIONS

Hahn, M. et al., "Coulometric titrations with an ion-exchange separation step" Fresenius' J. Anal. Chem. (1992) pp. 311-315 344(7-8)—Abstract Only.

(Continued)

*Primary Examiner* — Chester T Barry
(74) *Attorney, Agent, or Firm* — Stradley Ronon Stevens & Young, LLP

(57) ABSTRACT

A method of removing impurities from a urea solution comprising contacting the aqueous solution with an ion exchange resin and adsorbing the impurities from the urea solution, and the system therefore.

20 Claims, 3 Drawing Sheets

OTHER PUBLICATIONS

Sherman, John D., "IONSIV F-80 and IONSIV W-85: molecular sieve zeolite ammonium ion exchangers for removal of urea nitrogen" Artif. Kidney, Artif. Liver, Artif. Cells, Proc. McGill Artif. Organs Res. Unit Int. Symp. (1978), Meeting Date 1977, pp. 267-274 (Editor(s): Chang, Thomas Ming Swi. Publisher: Plenum, New York, NY—Abstract Only.

Shintani, H. et al.; "Determination of urea in blood by cation-exchange solid-phase extraction combined with HPLC" Bunseki Kagaku (1994), pp. 805-807 43(10)—Abstract Only.

Vasil'eva, T.A. et al, "Determination of urea in presence of hydrazine, ammonia and ammonium chloride" Zavod Lab. (1988) pp. 28-29 54(6)—Abstract Only.

* cited by examiner

METHOD FOR REMOVING IMPURITIES FROM A UREA SOLUTION

RELATED APPLICATION

This application claims the benefit of priority to U.S. Provisional Patent Application Ser. No. 60/966,617, filed on Aug. 29, 2007, the contents of which are incorporated in this application by reference.

FIELD OF THE INVENTION

The invention relates to methods and systems for removing impurities from a urea solution. Particular applicability can be found in removing processing contaminants and products resulting from hydrolysis and pyrolysis, including ammonia and resultant associated cations, from urea solutions.

BACKGROUND OF THE INVENTION

Urea is a nitrogen-containing chemical product that is used in many industries, including the agricultural, automotive, medical, biochemical, cosmetic, and pharmaceutical industries. In the pharmaceutical and cosmetic industries, urea may be used in such applications as a moisturizer, transdermal drug penetration enhancer, nail treatment, and osmotic diuretic. In the automotive industry, urea may be used as an after-treatment for diesel engines. Specifically, urea is used in a selective catalytic reduction ("SCR") process to eliminate oxides of nitrogen ("NOx") from lean-burn and diesel engines. The SCR process involves aqueous urea as a reducing agent injected and mixed with the engine's exhaust stream and catalytically reacted with the NOx. The NOx is reduced to $N_2$ and $H_2O$. Ammonia alone is also used in SCR, but the use of urea and ammonia together reduces SCR performance because competing reactions hamper NOx reduction.

Urea is produced from ammonia and carbon dioxide in an equilibrium reaction with an incomplete conversion of the reactants. Once produced, urea also hydrolyzes into ammonia and other impurities. As such, urea is often found unsuitable for many applications in the different industries. To stabilize the urea, additives, such as lactone in pharmaceutical and cosmetic applications, have been used, and to remove the ammonia in urea, catalysts of zeolite, metal hydroxides and metal cation loaded media have been used.

There are other unfavorable effects with urea impurities, such as ammonia, including unpleasant odors, health concerns, EPA concerns, pressure build-up from release of gas reactants, shelf-life restrictions, disposal issues for past shelf-life inventory, and potential for corrosion.

SUMMARY OF THE INVENTION

One aspect of this invention provides a method of removing soluble impurities from a urea solution comprising providing the urea solution with impurities; contacting the urea solution with an ion exchange resin having a plurality of crosslinked polymers, where each crosslinked polymer includes a functional group, at least one monomer and a crosslinker selected from acrylic monomers, methacrylate monomers and vinyl monomers; and adsorbing at least a portion of the impurities from the urea solution onto the ion exchange resin.

Another aspect of this invention provides a method of removing soluble impurities from a urea solution comprising providing the urea solution with impurities, where the impurities have ammonia and ammonia byproducts; contacting the urea solution with an ion exchange resin having styrene and divinylbenzene; and adsorbing at least a portion of the impurities from the urea solution onto the ion exchange resin.

A further aspect of this invention provides a system for removing soluble impurities from a urea solution comprising an ion exchange resin having a plurality of crosslinked polymers, where each crosslinked polymer includes an acid group, at least one monomer and a crosslinker selected from acrylic monomers, methacrylate monomers and vinyl monomers; and an absorption unit for contacting an amount of ion exchange resin with the urea solution.

DETAILED DESCRIPTION OF THE INVENTION

Figure 1:
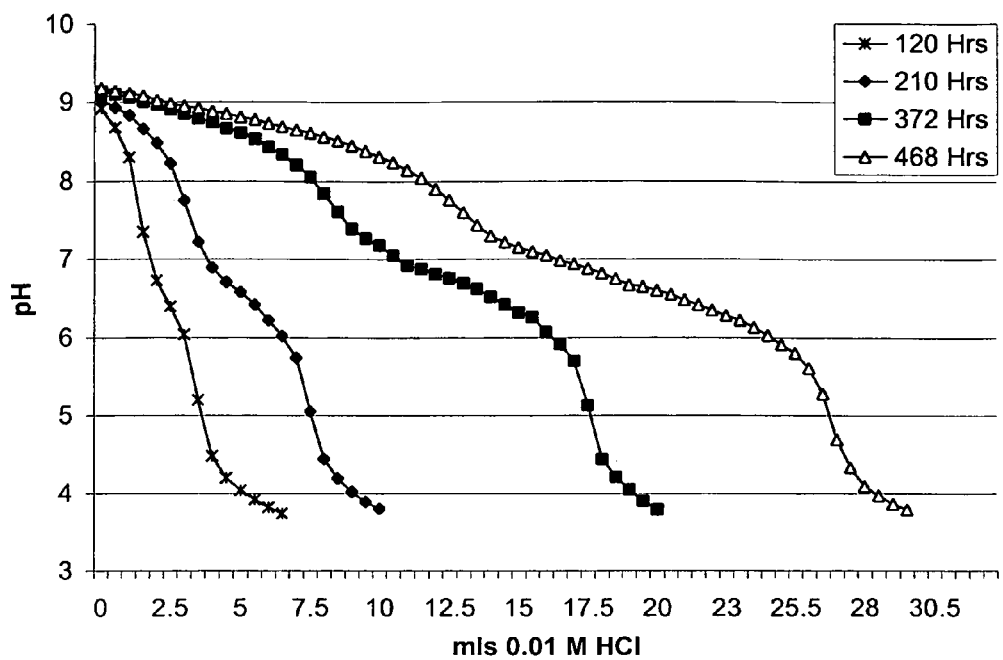
FIG. 1 shows a graph of pH versus mls 0.01 M (Molar) HCl for UL Commercial Grade 33.2% A&C Treatment over hours (Hrs) @ 120° F. (49° C.)

The invention provides a method of removing soluble impurities from a urea solution and a system therefore. Urea, itself, is a stable compound and is highly soluble in water. Solid urea, which is commonly available in prills or granules, is dissolved in water to make a urea solution. Preferably, the urea solution comprises up to 55 wt % urea. More preferably, the urea solution comprises 30-50 wt % urea. In one embodiment, the urea solution comprises 30-35 wt % urea. In another embodiment, the urea solution comprises 40-50% urea.

The re-crystallization temperature varies with concentration in water. For example, 32.5% urea solutions re-crystallize at about −11° C. and 50% urea solutions re-crystallize at about 17° C. The urea solutions remain liquid above the re-crystallization temperatures. At higher urea concentrations, urea will crystallize out of solution at higher temperatures.

Urea solutions are often contaminated with impurities that are formed during manufacturing, transportation, and storage of the urea solution. The impurities may be formed through hydrolysis, thermolysis, pyrolysis (prior to dissolving urea in water) or purposeful addition of processing aids, such as formaldehyde or urea-formaldehyde resins. For example, urea forms $NH_3$ through hydrolysis at temperatures above 30° C. Urea hydrolysis is represented by the following equation:

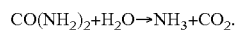

$$CO(NH_2)_2 + H_2O \rightarrow NH_3 + CO_2.$$

The first mole of ammonia release from the urea is not necessarily an impurity, but the second, third, and so on moles of ammonia react with intermediates to produce many side reactions with ammonia byproducts, including:

$CO(NH_2)_2 + H_2O \rightarrow NH_2COONH_4$ (ammonium carbamate)

$\rightarrow NH_3 + H_2CON$ (ammonia+isocyanic acid)

$\rightarrow (NH_4)_2CO_3$ (ammonium carbonate)

$\rightarrow (NH_4)HCO_3$ (ammonium bicarbonate)

$\rightarrow NH_4(+) + OCN(-)$ (ammonium cyanate).

Other impurities that may be formed include any other ammonium/urea complexes formed by hydrolysis, biuret, aldehyde, melamine, ammeline, ammelide, cyanuric acid, cyanic acid, cyamelide, and metals. The metals may include, but are not limited to, phosphorous (as phosphate), calcium, cadmium, lead, iron, copper, zinc, chromium, nickel, aluminum, manganese, magnesium, sodium, and potassium, and chlorine (as chloride). The specific impurities formed depend upon many factors, such as temperature, pressure, and time. For example, heat initiates various reactions in urea solutions that produce a multitude of impurities at various temperatures. In other words, at higher temperatures, hydrolysis rates are faster and more ammonia is formed. Thus, in one example, impurities in a solution of 50 wt % urea in water that re-crystallizes at approximately 17° C. are more rapidly formed when the solution is heated to a temperature above 17° C. to permit transport and allow for heat loss without jeopardizing equipment.

The impurities may be cationic or anionic. The specific impurities also depend upon the materials and equipment used to manufacture, store, or use the urea solution. For example, in the automotive industry, the source of metal impurities may be materials of construction for the manufacturing equipment, transfer equipment, bulk tanks, tank trucks and pumps.

Impurities in urea solution are often problematic. With ammonia, the urea solution has an unpleasant odor. The human threshold for ammonia is about 20 ppm. There may also be a pressure build-up with the release of ammonia and carbon dioxide gases generated by hydrolysis. Insoluble complexes may form due to contaminants and product formed by hydrolysis. The urea solution becomes affected by metals, such as calcium and magnesium, as carbonates and other intermediates are formed.

There are also health concerns with some impurities. For instance, ammonia gas is a severe respiratory tract irritant and exposure could lead to pulmonary edema and long-term respiratory system and lung disorders. High levels of airborne ammonia gas dissolve in moisture on the skin, forming corrosive ammonium hydroxide.

Urea solutions with impurities often have shorter shelf-lives and faster rates of hydrolysis, and disposal could be problematic if the impurity content deems the solutions as hazardous waste. The impurities could also cause corrosion of some materials that are not necessarily corrosive to urea.

To remove the soluble impurities from the urea solution, the urea solution is contacted with an ion exchange resin. The ion exchange resin, preferably, comprises a water soluble polymer. More preferably, the ion exchange resin has a plurality of crosslinked polymers, including a functional group, at least one monomer and a crosslinker. Examples of functional groups include acids and chelating resins. For cation resin, preferably, the functional group is hydrogen regenerated by sulfuric acid, sulfonic acid, sulfonate, carboxylic acid, carboxylate, sulfurous acid, phosphoric acid, phosphonate and/or hydrochloric acid. More preferably, the acid group is generated by sulfuric acid. For anion resin, the functional group is hydroxide regenerated by sodium hydroxide and/or potassium hydroxide. Epoxy polyamine polymer types, supplied in the free base form, may also be utilized in high flow rate applications.

The monomer is an ethylenically-unsaturated monomer. Examples include styrene, methylstyrene, ethylstyrene, ethylmethylstyrene, alkylstyrene, acrylonitrile, methacrylate, methylmethacrylate, methylacrylate, ethylmethacrylate, ethylacrylate, butylacrylate, methacrylic acid, acrylic acid, and vinylacetate and mixtures thereof.

Preferably, the crosslinker is an acrylic monomer, methacrylate monomer, or vinyl monomer. More preferably, the crosslinker is a vinyl aromatic, vinyl ether, vinyl ester, acrylic acid and/or methacrylic acid. Most preferably, the crosslinker is divinylbenzene (DVB), trivinylbenzene, divinyltoluene, divinylnaphthalene, divinylxylene, ethylvinylbenzene, acrylic acid and/or methacrylic acid.

The ion exchange resin may comprise particles or membranes. The ion exchange resin may be chosen based on a number of different parameters, including desired properties, cost, availability, and ease of use. It is the selection of the matrix type, type of polymer used for crosslinking, degree of crosslinking, and selection of the functional group that determine the physical properties of hardness, particle size, porosity, kinetic properties, and regeneration properties of the ion exchange resin.

The functional groups may be classified as strongly acidic (e.g., sulfonic acid groups), strongly basic (e.g., trimethylammonium groups), weakly acidic (e.g., carboxylic acid groups), weakly basic (e.g., amino groups), or specialized (e.g. chelating group). Preferably, the functional group is a sulfonic acid, sulfonate, carboxylic acid, carboxylate, sulfuric acid, sulfurous acid, phosphoric acid, phosphonate, hydrochloric acid, or chelating group.

Preferably, the ion exchange resin is a cation exchange resin in a hydrogen form or an anion exchange resin in a hydroxide form, but may be any ion exchange resin that is able to adsorb ammonia and exchange for carbonates and/or release carbon dioxide. If a strong cation resin is used, ammonium is absorbed, leaving carbonic acid. The carbonic acid will vent as carbon dioxide based on the temperature and pressure of the solution. Weak cation resins will typically absorb the anion in the solution. Strong anion & weak anion resins absorb the anion in the solution. In either case, no carbonic acid is in the solution and thus, there is no release of carbon dioxide.

To remove the anion that results from the ammonium ion formation, an anion exchange resin may be used. The anion is retained on the anion exchange resin and a hydroxide ion is exchanged into solution. The cation exchange resins absorb the ammonium ions and other cations and replace them with H+. The anion exchange resins absorb the carbonates and other anions and replace them with OH−. With either ion exchange resin, the ion exchange resin may be regenerated for further use.

Anion exchange resins include divinylbenzene-styrene copolymers, phenolformaldehydes, acrylics, and epoxies. The polymer structure is typically styrene crosslinked with DVB with the ionic form as hydroxide. Various acrylic polymers, phenolformaldehydes, and epoxies are other types of polymer backbones that may be used in making an anion resin (insoluble). These anion resins made in the hydroxide ionic form will function as well.

In one embodiment, the ion exchange resin comprises a strong acid cation exchange resin, for example, crosslinked polymers having a styrene backbone with a divinylbenzene crosslinker, activated with sulfuric acid. A preferred ion exchange resin is a styrene-divinylbenzene resin. In a preferred embodiment, the amount of divinylbenzene in the polystyrene will be between 8 to 10 wt % by weight.

In another embodiment, the ion exchange resin comprises a weak acid cation resin having a matrix structure that is polyacrylic or polymethacrylic or has phenol-formaldehyde. The various possible types of matrices and the degree of crosslinking are used to vary the physical properties and osmotic stability.

The ion exchange resin may also be chosen based on the particle size of the crosslinked polymer and total exchange capacity, which measures the performance of the functional groups. In one embodiment, the ion exchange resin has a particle size of between 16-60 mesh with <2% through a 16 mesh and <1% greater than a 60 mesh. In another embodiment, a strong acid gel may have a total exchange capacity of between 1.6 to 2.2 mEq/ml or 35 to 48 kg/ft$^3$; a strong acid gel may have a total exchange capacity of between 1.6 to 2.2 mEq/ml or 35 to 48 kg/ft$^3$; a weak acid gel may have a total exchange capacity of between 2.1 to 4 mEq/ml or 45.9 to 87.4 kg/ft$^3$; a strong base gel may have a total exchange capacity of between 0.95 to 1.45 mEq/ml or 20.8 to 31.7 kg/ft$^3$; and a weak base gel may have a total exchange capacity of between 1.6 to 3 mEq/ml or 35 to 65.6 kg/ft$^3$.

The ion exchange resins may be also used alone or may be used with zeolite concurrently or in sequence. The ion exchange resin may also be used with other anion and cation exchange resins for removal of impurities. Mixed blends of anion and cation resins may be utilized. The ratio of the mix should be such that both types are exhausted simultaneously, but not necessarily. The mix would need to be regenerated when either type is exhausted.

Depending on the desired resultant pH of the urea liquor or specific impurities that are selected for removal, the solution may be passed through anion exchange resin (increasing the pH) and then through cation exchange resin (reducing the pH) for a final pH as low as 2 or reverse the sequence for a pH as high as 12.5. A "mixed bed" of a desired ratio, typically, 60% anion and 40% cation exchange resin, may be utilized for complete removal of soluble impurities. The ratio may be adjusted for simultaneous exhaustion or other desired results.

Urea solutions may be passed through ion exchange resins in various sequences to determine the composition of the final product. The ion exchange resin(s) adsorb at least a portion of the impurities from the urea solution onto the ion exchange resin. Preferably, at least 50% of the impurities are removed; more preferably, at least 75% of the impurities are removed; and most preferably, at least 90% of the impurities are removed. In one embodiment, where the impurities include ammonia, substantially all, i.e., at least 99%, of the ammonia is removed. In some applications, up to 99.6%, 99.7%, 99.8%, 99.9%, and even up to 100% may be removed.

In one embodiment of the invention, the urea solution contains at least ammonia as an impurity, where hydrolysis produces other impurities, including ammonium bicarbonate, ammonium carbonate, isocyanic acid, ammonium carbamate, and carbon dioxide. As the ammonia is generated, the pH of the urea solution increases. However, there is no odor if the ammonia is removed, i.e., the pH is kept below pH=8. One aspect of the invention is that the pH is lowered by 1) absorption of the ammonia by the ion exchange resin and 2) release and solubility of carbon dioxide resulting in carbonic acid.

As the ammonia and any other impurities are removed, the urea solution is purified. Pure urea solutions prepared in deionized water are essentially non-conductive. As urea solutions hydrolyze or are contaminated, the solution will become more conductive. Urea solutions that have high conductivity and are passed through both anion (OH−) and cation (H+) resin return to a non-conductive state. The removal of conductive impurities also permits an additional monitoring tool for processing. The urea solution may be purified at any stage of its use, including in its storage container and in an apparatus before or where it is used.

The purified urea may be used in the automotive, medical, biochemical, and pharmaceutical industries. For example, the ion exchange resin may be added to fuel tanks, service stations, storage containers, devices for transferring urea on site at a service station or production facility and units prior to charging a vehicle with urea or maintain their bulk supply. Purified urea with ammonia impurities of under 2000 ppm may have an extended shelf-life of up to 2 years under room temperature.

In one embodiment in the automotive industry, purified urea is utilized in SCR. With no ammonia in the purified urea, there are no competing reactions to hamper NOx reduction and thus, more NOx is converted to $N_2$ and $H_2O$.

The invention also includes a system for removing any soluble impurities from the urea solution. This system comprises the ion exchange resin, an absorption unit for contacting the ion exchange resin with the urea solution and, optionally, a regeneration unit for regenerating the ion exchange resin. Exemplary absorption units include fixed beds, countercurrent columns, and slurry units. One embodiment of the invention includes a container, having a column packed with the ion exchange resin for removing the impurities from the urea solution. The ion exchange resin may comprise particles and/or membranes.

The following examples are presented to illustrate the method and composition of the invention. These examples are intended to aid those skilled in the art in understanding the present invention. The present invention is, however, in no way limited thereby.

The following examples are presented to illustrate the invention. In the examples and throughout the specification, the following abbreviations have been used:
m/m is by mass;
cc is cubic centimeter;
ft is feet;
l is liter; ml is milliliter;
g is gram; kg is kilogram;
$m^3$ is cubic meters;
mEq is milliequivalents;
mls is milliliters;
mol is moles;
ppm is parts per million; and
wt is weight.

Test Methods

Aldehyde: Determination of the content of free and bound aldehyde, calculated as formaldehyde, was done using the standard procedure described in ISO/DIS 22241-2, Annex F.

Alkalinity: Determination of alkalinity was done by weighing the mass of a homogenous sample to 0.05 g and putting the sample into a 150 ml beaker filled with deionized water. The content of the beaker was titrated with hydrochloric acid solution (0.01 mol) under stirring from pH=7.5 to an endpoint of pH=5.7. The alkalinity, expressed as percentage by mass of ammonia (NH3), is calculated by the formula:

$$W(NH3) = (V \times 0.017)/Ms$$

where
W(NH3) is the alkalinity, calculated as ammonia (% (m/m));
V is the volume of the hydrochloric acid solution used for the titration (ml); and
Ms is the mass of the test portion (g).

Ammonia Odor: Odor was measured using olfactory senses.

Ammonia Removal: The amount of ammonia in the urea solution was measured by determining the alkalinity of the urea solution calculated as ammonia according to the standard procedure described in ISO/DIS 22241-2, Annex D.

Biuret: Determination of the biuret content was done using the standard procedure described in ISO/DIS 22241-2, Annex E.

Conductivity: Conductivity was measured with a Corning COND/TDS meter or equivalent water testing conductivity meter.

pH: pH was measured with a calibrated, pH meter from VWR Scientific Products Corporation, Westchester, Pa., Model 8000 pH/Temp Meter.

Trace Elements Content: Determination of Aluminum, Calcium, Chromium, Copper, Iron, Potassium, Magnesium, Sodium, Nickel, and Zinc was done using the standard procedure described in ISO/DIS 22241-2, Annex I.

Titrations and Titration Curves: These were determined the same as Alkalinity, except pH readings were recorded after each of 0.5 ml of 0.01 Molar hydrochloric acid. Results were graphed, pH vs. mls 0.01 M HCl. 2.0 gram samples of urea solutions were tested.

Urea Content: Determination of urea content was done using the standard procedure described in ISO/DIS 22241-2, Annex B, or Annex C.

EXAMPLES

Example 1

500 ml of urea solution having 32.5 wt % urea and 2,000 ppm ammonia was passed through a cation exchange resin having a styrene backbone with divinylbenzene and activated with sulfuric acid. The resultant urea solution had less than 1 ppm ammonia. The ratio of required resin to ammonia in the urea solution was calculated to be 1 cc resin per 9.5 ml urea liquor at 4,000 ppm ammonia.

Comparative Example 500 ml urea solution having 32.5 wt % urea and 2,000 ppm ammonia was passed through zeolite The resultant urea solution had 1,200 ppm ammonia, which was an approximately 40% reduction.

Example 2

A 5,000 gallon (18,927 liter) tank was used to receive 3,170 (12,000 liters) gallons of urea liquor with 50 wt % urea. Cold deionized water was added to the tank to produce approximately 5,000 gallons (18,927 liters) of urea solution having 32.5 wt % urea. The urea solution contained 1,100 ppm as ammonia. 30 cubic feet (0.85 $m^3$) of cation exchange resin was charged into a reactor fitted with a pressure gauge and exhaust line fitted with a operable valve. The cation exchange resin had a styrene backbone with divinylbenzene activated with sulfuric acid and was in the form of beads having a density of approximately 0.8 g/cc. The urea solution was pumped through the reactor in approximated 1.5 hours and then stored in a 5,800 gallon (21,955 liter) storage tank. The urea solution in the storage tank has a pH of 5.79 and no ammonia odor.

While the invention has been described in detail and with reference to specific embodiments thereof, it will be apparent to one skilled in the art that various changes and modifications can be made therein without departing from the spirit and scope thereof. Thus, it is intended that the invention covers the modifications and variations of this invention provided they come within the scope of the appended claims and their equivalents.

Example 3

Figure 2:
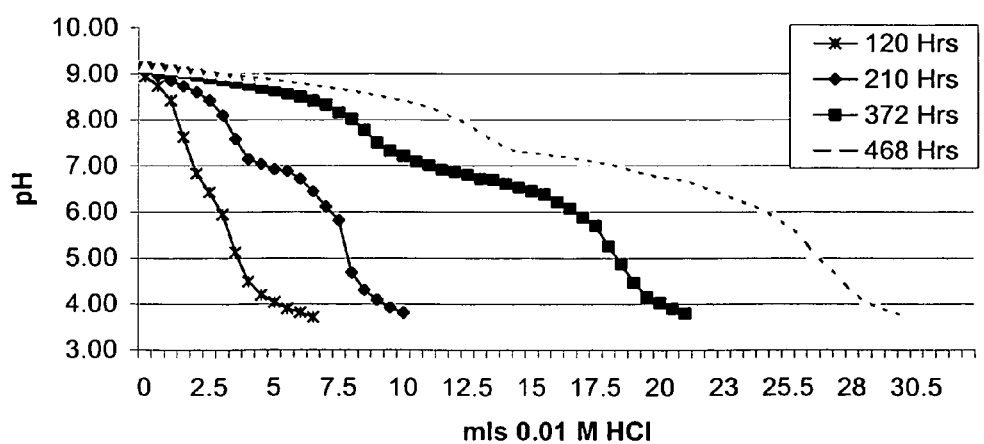
FIG. 2 shows a graph of pH versus mls 0.01 M HCL for USP Grade @ 32.5% over. hours (Hrs) @ 120° F. (49° C.)
Figure 3:
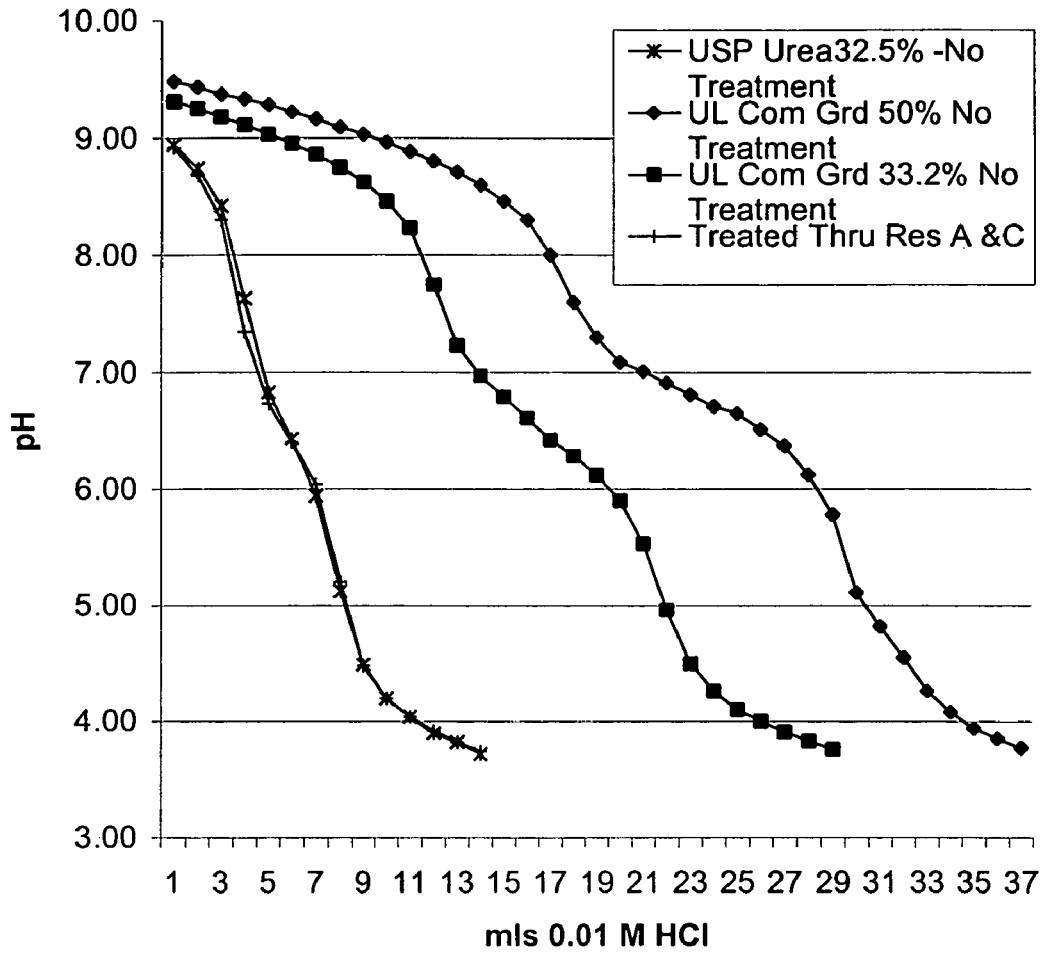
FIG. 3 shows a graph of pH versus mls 0.01 M HCl for urea samples stored for 120 hours @ 120° F. (49° C.)
Figure 4:
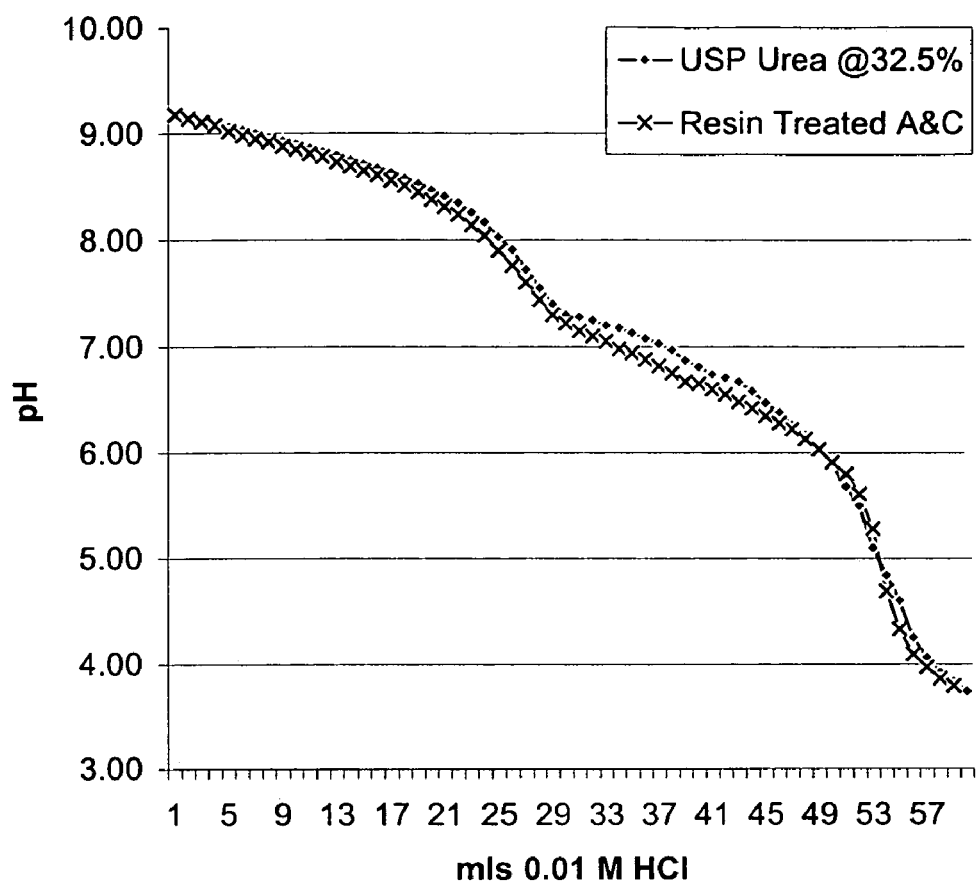
FIG. 4 shows a graph of pH versus mls 0.01 M HCl for urea stored for 468 hours @ 120° F. (49° C.).

1 liter of technical grade 33.2% urea liquor was produced by dilution of 50% urea liquor with 803 ppm ammonia passed through anion resin. Resultant pH was 12.5. The urea liquor was then passed through cation resin with a resultant pH of 4.5. The sample was placed in an oven at 120° F. (49° C.). A sample of USP grade (i.e., pharmaceutical grade) urea solution (certified to be 99.67% urea) diluted to 32.5% with deionized water was put into the oven for comparison. The samples were pulled after 120, 210, 372, 468 hours at 120° F. (49° C.), cooled to 68° F. (20° C.), and a full titration curve was generated from starting pH to a pH of 3.8 for each. Results are shown in FIGS. 1 and 2.

The stability of the urea liquor passed through the anion and cation resin show equal to better oven stability as USP grade urea, thereby providing maximum stability.

Graph 3 illustrates the titration curves for samples stored for 120 hours at 120° F. (49° C.) of USP urea @ 32.5%, UL (Urea Liquor) Commercial Grade 50%, UL Commercial Grade 33.2%, and a treated sample through anion and cation resin. Graph 4 shows a comparison between the USP 32.5% urea liquor vs. the treated sample of Commercial grade UL 32.5% stored at 120° F. (49° C.) for 468 hours.

Example 4

An approximate quantity of 5,000 gallons (18,927 liters) of 50% urea liquor, stored at a location, in excess of one year, was received for treatment and testing. The sample was pulled and was subject to no treatment. This original sample was submitted for analytical testing. A second sample, Sample A, was passed through strong anion resin in a set-up similar to Example 1. This sample was pulled and submitted for analytical testing. A third sample that was previously treated with strong anion resin was treated with strong cation resin in a set up similar to Example 1. This sample, Sample A/C, was pulled and submitted for analytical testing. Results are shown in Table 1.

TABLE 1

| Characteristics | Test Method | Original | Sample A | Sample A/C |
|---|---|---|---|---|
| Urea Content, m/m | Annex C | 35 | 35 | 35 |
| Ammonia, ppm | Annex D | 2,900 | not tested | 0 |
| Biuret, ppm | Annex E | 0.34 | 0.10 | 0.08 |
| Aldehydes, ppm | Annex F | 46.3 | 24.84 | 25.13 |
| Phosphate ($PO_4$), ppm | Annex H | 1.29 | 0.21 | Not tested |
| Calcium, ppm | Annex I | 0.32 | <0.01 | <0.01 |
| Iron, ppm | Annex I | 0.25 | <0.01 | <0.01 |
| Copper, ppm | Annex I | 0.19 | 0.02 | <0.01 |
| Zinc, ppm | Annex I | 0.19 | <0.01 | <0.01 |
| Chromium, ppm | Annex I | 0.1 | <0.01 | <0.01 |
| Nickel, ppm | Annex I | 0.12 | <0.01 | <0.01 |
| Aluminum, ppm | Annex I | 0.09 | <0.01 | <0.01 |
| Magnesium, ppm | Annex I | 0.08 | 0.02 | <0.01 |
| Sodium, ppm | Annex I | 0.32 | <0.01 | <0.01 |
| Potassium, ppm | Annex I | 0.44 | <0.01 | <0.01 |

Example 5

Sample A and Sample A/C from Example 4 were tested for conductivity.
Results:
Sample-Original=7.23 millisiemens
Sample-A/C=<1 microsiemens Example 6

Each of the resins used in the removal of impurities of urea liquor were able to be fully regenerated to their hydrogen or hydroxide form by conventional processes currently utilized commercially. No abnormal degradation of the polymers, decrease in exchange capacity, or fouling of the resins was detected.

The invention claimed is:

1. A method of removing soluble impurities from a urea solution comprising:
providing the urea solution with impurities;
contacting the urea solution with an ion exchange resin having a plurality of crosslinked polymers, each crosslinked polymer including a functional group, at least one monomer and a crosslinker selected from acrylic monomers, methacrylate monomers and vinyl monomers;
adsorbing at least a portion of the impurities from the urea solution onto the ion exchange resin; and
removing substantially all of an amount of ammonia from the urea solution.

2. The method of claim 1 further comprising:
regenerating the ion exchange resin for further use.

3. A method of removing soluble impurities from a urea solution comprising:
providing the urea solution with impurities;
contacting the urea solution with an ion exchange resin having a plurality of crosslinked polymers, each crosslinked polymer including a functional group, at least one monomer and a crosslinker selected from acrylic monomers, methacrylate monomers and vinyl monomers;
contacting the urea solution with zeolite; and
adsorbing at least a portion of the impurities from the urea solution onto the ion exchange resin.

4. The method of claim 1 wherein the providing comprises:
dissolving urea in a solution; and
forming the impurities in the solution.

5. The method of claim 1 wherein the ion exchange resin comprises at least one of a cation exchange resin in a hydrogen form and an anion exchange resin in a hydroxide form.

6. The method of claim 1 wherein the ion exchange resin comprises particles having a screen size distribution of 16 to 60 mesh.

7. The method of claim 1 wherein the ion exchange resin comprises a styrene divinylbenzene resin.

8. The method of claim 1 wherein the crosslinker comprises at least one of divinylbenzene, trivinylbenzene, divinyltoluene, divinylnaphthalene, divinylxylene, ethylvinylbenzene, acrylic acid, and methacrylic acid.

9. The method of claim 1 wherein the functional group comprises at least one of a sulfonic acid, sulfonate, carboxylic acid, carboxylate, sulfuric acid, sulfurous acid, phosphoric acid, phosphonate, hydrochloric acid, and chelating group.

10. The method of claim 1 wherein the at least one monomer comprises an ethylenically-unsaturated monomer selected from the group consisting of styrene, methylstyrene, ethylstyrene, ethylmethylstyrene, alkylstyrene, acrylonitrile, methacrylate, methylmethacrylate, methylacrylate, ethylmethacrylate, ethylacrylate, butylacrylate, methacrylic acid, acrylic acid, vinylacetate and mixtures thereof.

11. The method of claim 1 wherein the impurities comprise at least one of ammonia, ammonium carbamate, ammonium carbonate, ammonium bicarbonate, ammonium cyanate, chloride, biuret, isocyanic acid, melamine, ammeline, ammelide, cyanuric acid, cyanic acid, cyamelide, aldehyde, phosphate, calcium, cadmium, lead, iron, copper, zinc, chromium, nickel, aluminum, manganese, magnesium sodium, and potassium.

12. A urea solution substantially free of ammonia prepared from the method of claim 1.

13. The method of claim 3 wherein the ion exchange resin comprises at least one of a cation exchange resin in a hydrogen form and an anion exchange resin in a hydroxide form.

14. The method of claim 3 wherein the ion exchange resin comprises a styrene divinylbenzene resin.

15. The method of claim 3 wherein the crosslinker comprises at least one of divinylbenzene, trivinylbenzene, divinyltoluene, divinylnaphthalene, divinylxylene, ethylvinylbenzene, acrylic acid, and methacrylic acid.

16. The method of claim 3 wherein the functional group comprises at least one of a sulfonic acid, sulfonate, carboxylic acid, carboxylate, sulfuric acid, sulfurous acid, phosphoric acid, phosphonate, hydrochloric acid, and chelating group.

17. The method of claim 3 wherein the at least one monomer comprises an ethylenically-unsaturated monomer selected from the group consisting of styrene, methylstyrene, ethylstyrene, ethylmethylstyrene, alkylstyrene, acrylonitrile, methacrylate, methylmethacrylate, methylacrylate, ethylmethacrylate, ethylacrylate, butylacrylate, methacrylic acid, acrylic acid, vinylacetate and mixtures thereof.

18. The method of claim 3 wherein the impurities comprise at least one of ammonia, ammonium carbamate, ammonium carbonate, ammonium bicarbonate, ammonium cyanate, chloride, biuret, isocyanic acid, melamine, ammeline, ammelide, cyanuric acid, cyanic acid, cyamelide, aldehyde, phosphate, calcium, cadmium, lead, iron, copper, zinc, chromium, nickel, aluminum, manganese, magnesium sodium, and potassium.

19. A urea solution substantially free of ammonia prepared from the method of claim 3.

20. The method of claim 1 further comprising:
contacting the urea solution with zeolite.

* * * * *